(12) United States Patent
Seligman et al.

(10) Patent No.: US 11,759,543 B2
(45) Date of Patent: *Sep. 19, 2023

(54) MULTI-COMPONENT FRAME FOR USE IN AN ORTHOPEDIC DEVICE

(71) Applicant: OSSUR ICELAND EHF, Reykjavik (IS)

(72) Inventors: Scott Seligman, Foothill Ranch, CA (US); Jared Olivo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 18/065,550

(22) Filed: Dec. 13, 2022

(65) Prior Publication Data
US 2023/0105907 A1 Apr. 6, 2023

Related U.S. Application Data

(63) Continuation of application No. 16/437,413, filed on Jun. 11, 2019, now Pat. No. 11,547,774.
(Continued)

(51) Int. Cl.
*A61L 15/12* (2006.01)
*A61F 5/01* (2006.01)
(Continued)

(52) U.S. Cl.
CPC .......... *A61L 15/125* (2013.01); *A61F 5/0123* (2013.01); *A61L 15/08* (2013.01); *A61L 15/14* (2013.01)

(58) Field of Classification Search
CPC ........ A61L 15/125; A61L 15/08; A61L 15/14; A61F 5/0123; A61F 5/0125; A61F 5/01;
(Continued)

(56) References Cited

U.S. PATENT DOCUMENTS 3,350,719 A 11/1967 McClure
4,241,730 A 12/1980 Helfet
(Continued)

FOREIGN PATENT DOCUMENTS

EP 1829507 B1 12/2000
EP 2802298 A1 11/2014
(Continued)

OTHER PUBLICATIONS

International Search Report and Written Opinion from PCT Application No. US2019/036480, dated Dec. 4, 2019.
(Continued)

*Primary Examiner* — Michelle J Lee
*Assistant Examiner* — Daniel A Miller
(74) *Attorney, Agent, or Firm* — WORKMAN NYDEGGER

(57) ABSTRACT

A multi-component frame includes a first component made from a rigid structural material and a second component connected to at least an end portion the first component. The first component is constructed from a metal or metal alloy, and the second component is constructed from a material different from the first component. The first and second components form at least part of a length of the multi-component frame.

18 Claims, 8 Drawing Sheets

Related U.S. Application Data

(60) Provisional application No. 62/683,152, filed on Jun. 11, 2018.

(51) Int. Cl.
*A61L 15/08* (2006.01)
*A61L 15/14* (2006.01)

(58) Field of Classification Search
CPC ........ A61F 5/0109; A61F 5/0111; A61F 5/26; A61F 5/30; A61F 5/0104; A61F 5/0106; A61F 5/0118; A61F 5/013; A61F 5/373; A61F 2005/0139; A61F 2005/0144; A61F 2005/0137; A61F 2005/0172; A61F 2005/0197; A61F 2005/0176; A61F 2005/0179; A61F 2/78; A61F 2/7812; A61F 2/80; A61F 2/461; A61F 2/30965; A61F 2002/7831; A61F 2002/7875; A61F 2002/4495; A61F 2002/5055; A61F 2002/30935; A63B 71/08; A63B 7/1225; A61B 17/75; A61B 17/64; A61H 1/024; A61H 1/0255
USPC .................................. 602/16, 12, 23, 26
See application file for complete search history.

(56) References Cited

U.S. PATENT DOCUMENTS

| | | |
|---|---|---|
| 4,271,831 A | 6/1981 | Deibert |
| 4,628,916 A | 12/1986 | Lerman et al. |
| 5,042,464 A | 8/1991 | Skwor et al. |
| 5,336,161 A | 8/1994 | Lengyel |
| 5,554,104 A * | 9/1996 | Grim ............... A61F 5/0125 602/8 |
| 5,608,599 A | 3/1997 | Goldman |
| 5,658,243 A | 8/1997 | Miller et al. |
| 5,891,068 A | 4/1999 | Kenney |
| 5,947,913 A | 9/1999 | Palumbo |
| 6,331,169 B1 | 12/2001 | Bastyr et al. |
| 6,527,733 B1 | 3/2003 | Ceriani et al. |
| 7,410,471 B1 | 8/2008 | Campbell et al. |
| 7,597,674 B2 | 10/2009 | Hu et al. |
| 7,749,183 B2 | 7/2010 | Ingimundarson et al. |
| 8,043,244 B2 | 10/2011 | Einarsson et al. |
| 8,657,772 B2 | 2/2014 | Einarsson |
| 8,936,560 B2 | 1/2015 | Lunau et al. |
| 2004/0054311 A1* | 3/2004 | Sterling ............... A61F 5/0123 602/26 |
| 2005/0209541 A1 | 9/2005 | Kenney |
| 2005/0240135 A1* | 10/2005 | Hoffmeier ............ A61F 5/0123 602/26 |
| 2008/0195013 A1 | 8/2008 | Ingimundarson et al. |
| 2008/0208095 A1 | 8/2008 | Kazmierczak et al. |
| 2010/0121242 A1 | 5/2010 | Chiang |
| 2010/0168627 A1 | 7/2010 | Einarsson et al. |
| 2011/0167546 A1 | 7/2011 | Olson |
| 2012/0016283 A1 | 1/2012 | Hollister et al. |
| 2015/0320581 A1 | 11/2015 | Causse |
| 2016/0051389 A1 | 2/2016 | Seligman |
| 2016/0206448 A1* | 7/2016 | Klutts ................. A61F 5/01 |
| 2016/0250058 A1 | 9/2016 | Frangi et al. |
| 2016/0302955 A1* | 10/2016 | Siddiqui ............ A61F 5/0123 |
| 2018/0116852 A1 | 5/2018 | Petursson et al. |
| 2019/0374671 A1 | 12/2019 | Seligman et al. |

FOREIGN PATENT DOCUMENTS

| | | |
|---|---|---|
| JP | H11-504530 A | 4/1999 |
| WO | 9620659 A1 | 7/1996 |
| WO | 2005107659 A2 | 11/2005 |
| WO | 2013052358 A1 | 4/2013 |
| WO | 2019241201 A1 | 12/2019 |

OTHER PUBLICATIONS

International Search Report and Written Opinion from PCT Application No. PCT/US2021/020995, dated Jun. 11, 2021.

* cited by examiner

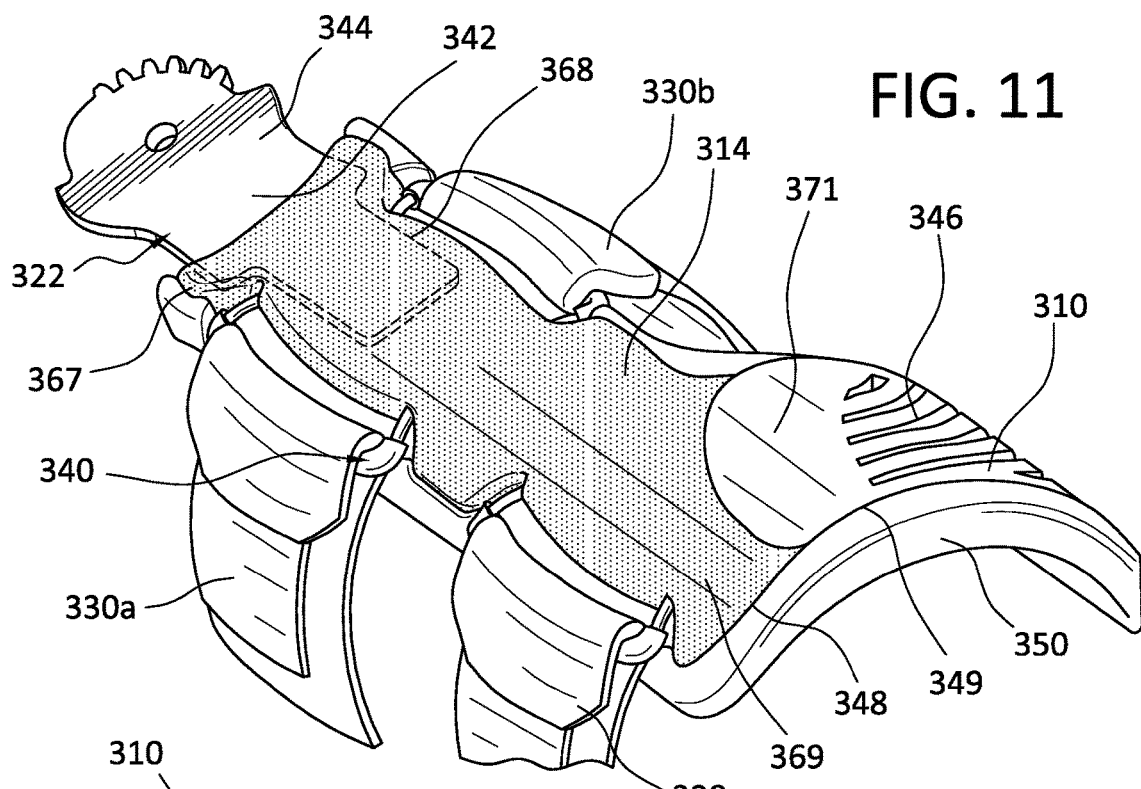
FIG. 11
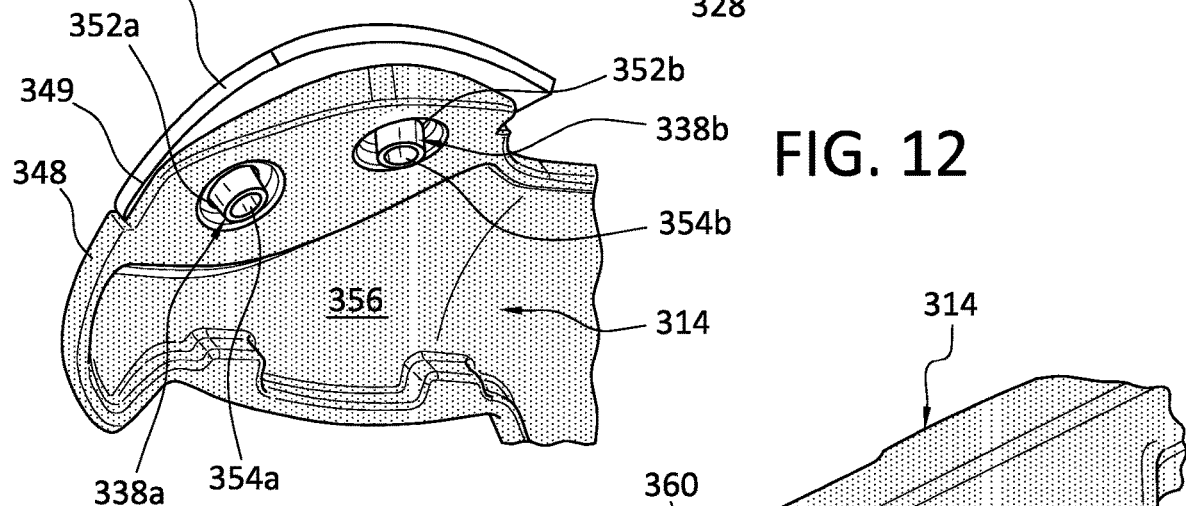
FIG. 12
FIG. 13

MULTI-COMPONENT FRAME FOR USE IN AN ORTHOPEDIC DEVICE

FIELD OF THE DISCLOSURE

The disclosure relates to a frame for an orthopedic device, and more specifically to a multi-component frame formed from layers or sections of different materials arranged in a predetermined configuration, and means for attaching features, such as straps, to a structure in an orthopedic device.

BACKGROUND

Orthopedic devices or braces comprise a broad range of structures and devices used for supporting or stabilizing a joint when worn on the body of a user. Orthopedic braces may serve in either preventive or remedial roles. In the preventive role, the orthopedic brace can provide additional support, stability, and protection to a healthy joint to prevent or minimize injury to the joint due to undue stress. In the remedial role, the orthopedic brace can support and strengthen a joint weakened due to injury or infirmity, and reinforce the vulnerable joint to prevent further injury, to correct or assist the infirmity, or to facilitate healing of the joint.

A predominant orthopedic brace is a knee brace, which is used to stabilize the knee by preventing excessive movement of the knee or facilitate the motion of the knee. Many knee braces comprise a frame and have hinges on at least one of the lateral and medial sides of the knee joint. Straps are used to secure the brace to the leg or knee. An injured knee can be fit with an "off-the-shelf" brace or with a "custom-fit" brace, with the selection of the brace depending on the size and shape of an individual's leg. A clinician may further form either type of braces by providing the frame with malleable materials to customize the frame to the user.

As shown in FIG. 1, an exemplary knee brace 10 typically includes a frame that comprises at least one support member 12, 14. When there are multiple support members 12, 14, the knee brace 10 may include rotational hinges 16 that assist and control the movement of the limb. Suitable straps 20 depend from strap attachments 22 and may maintain the knee brace 10 on the limb, and other features such as pads 18 may relieve the pressure of the knee brace 10 on the limb and surrounding areas.

Many knee braces reduce knee instability following an injury, counteract fatigue, and treat the impairment of the knee, particularly if the knee has damaged ligaments. Braces may be recommended for walking, skiing, running, twisting, pivoting, or jumping activities. Besides providing increased stability to the knee, knee braces may also decrease the risk of injuring the knee or leg or may assist the knee. One way of protecting the knee is by including attachments such as a patella-protector assembly which may be secured onto the knee brace and configured to operate to protect the patella from impact during physical activities.

To maximize its supportive, protective, and comfort-related aspects, it is desirable that a knee brace securely and precisely fit the leg of the user. While custom-fit braces are made to intimately conform to the precise geometry and dimensions of a leg of a user, it is typical for the geometry and dimensions of the leg to change over time due to weight change, muscle change, inflammation, medical conditions, or other factors, requiring even a custom-fit brace to accommodate many geometries of the leg. As for off-the-shelf braces, these braces must be configurable to generally suit many leg geometries despite the geometry of a particular leg. There is a need for braces that accommodate a user's dynamic dimensions.

Existing braces further fail to account for the geometrical and dimensional variations between different parts of a leg, e.g., the difference in shape between the calf and the shin. Certain areas of the leg require more accommodation from the brace than others, but most braces have only flat frame components and thus fail to address this need.

In recognizing the need for effective knee braces, various knee braces have been introduced into the marketplace. Such knee braces, however, have generally comprised relatively heavy, bulky apparatuses that fail to provide ventilation and to evenly distribute pressure from the brace on the leg of the user. Many contemporary braces are deficient because the braces are constructed in a manner that lacks or does not consistently provide adjustment features for forming a firm, comfortable, and secure interface between the unique and dynamic dimensions of the leg and knee of the user and the brace. Because of these drawbacks, many knee braces detract from the user's endeavor.

For example, some strap supports may be deficient because they add to the brace's bulk by jutting out from the frame with a rigid strap support structure. These features may cause discomfort for a user, increasing the size, profile, and weight of the brace, increasing the cost to a user and making the brace cumbersome to use because of the brace's larger size. Such straps may further increase the risk of damage to the brace and discomfort for a user if, for example, the outwardly jutting straps catch on objects or clothing.

Braces may need to incorporate auxiliary structures such as sensors, padding, structural support, or aesthetic features into the frame. Existing braces, which utilize flat metal structures, do not have a convenient disposition for such auxiliary structures and thus the auxiliary structures must attach or append to the brace, often in uncomfortable, unsightly, and maintenance-intensive ways. This further increases the bulk of the brace.

The features of the present disclosure are provided in recognition of the need for orthopedic braces and components in both custom-fit and off-the-shelf braces to achieve superior functional performance characteristics while being comfortable to the user when worn and adapting to the user's dynamic dimensions. This recognition is realized with the embodiments described in the disclosure.

SUMMARY

The multi-component frame of the disclosure addresses the problem of existing frames being bulky, which hinders patient compliance and use. The multi-component frame of the disclosure increases strength over known frame systems and leads to a streamlined arrangement with improved concealment of padding, cushioning, and skin-facing layers. These layers are located generally within a concavity of the multi-component frame. These improved features contribute to the multi-component frame being more lightweight, comfortable, and low-profile over known devices without sacrificing desired strength.

As an alternative or besides multi-component layers, the multi-component frame may comprise multi-component segments juxtaposed or abutting one another along a length or a course of a frame assembly. For example, a frame assembly may be defined as having a continuous length between end points, such as at hinges, although it is generally contoured to a limb upon which it is secured. The frame assembly comprising a multi-component frame has at least two segments juxtaposed, abutting or overlapping one another at their end portions along the length and may correspond to different sides of the limb, or be adapted to different degrees of stress the segments may undergo at a particular location of the limb during activity and inactivity.

By "multi-component," it should describe the multi-component frame as comprising layers or structural features formed from different materials used for strengthening, concealing, contouring, padding, and other intended benefits, particularly in the art of orthopedic devices. The multi-component frame includes at least two layers or segments of different materials, adjacent to one another along at least a portion of their length or end portions in predetermined locations and providing complementary structural benefits.

The multi-component frame may start with a first or base component of a metal frame upon which supplemental components may be attached. While the metal frame may be sufficiently strong to withstand forces exerted by or imposed upon a user during use, the strength may be further enhanced by adding structural components, such as fiber-reinforced layers or inserts attached to the metal frame. The metal frame may be provided with padding or cushioning layers adapted for being adjacent to the skin and anatomy of the user.

The metal frame may be provided with a curved or concave profile, with the concavity located to face the user, and in which the additional components are received. The curved profile of the metal frame offers by itself enhanced mechanical strength over a conventional flat metal frame, and can easily be enhanced with additional layers of structural materials located within a cavity formed by the curved or concave profile.

In an exemplary embodiment, the entire or near entire metal frame is hollow or has a concave cross-section. An advantage of a metal frame is that it can be malleable. While orthopedic devices may be made out of carbon fiber, plastic or other suitable structural materials where an entire frame is hollow or concave, these frames are not malleable and thus are not adaptable to a user's unique and dynamic dimensions and needs. Carbon fiber is brittle, and making a thin low-profile carbon fiber frame is difficult and potentially hazardous to the user. The frame often is thick in structure, and may deleteriously add undesirable weight.

Most orthopedic devices having a metal frame defined with a flat cross-section because it is obtained with little difficulty during the manufacturing process. Some devices are molded from carbon fiber and define a frame with a hollow oval cross-section. However, such devices must be sufficiently bulky to balance the drawbacks of using carbon fiber, such as brittleness. There are other devices having frames molded out of metal, carbon fiber or plastic with oval or partial oval cross-sections, yet such configurations sacrifice either a desired strength, malleability, or weight.

A metal frame with a continuous concave cross-section provides both high strength and reduced weight and profile, and is malleable and not brittle. The expression "malleable" has its ordinary meaning of being hammered, pressed, or otherwise formed permanently out of shape without breaking or cracking. Traditional flat knee brace frames are made by rolling a flat piece of metal around a mandrel to create a shape to fit the leg. Such an arrangement or process cannot be done with a concave cross-section because the metal would buckle, crease, and fold on itself. According to this embodiment with a metal frame, a solution is provided which solves these design and manufacturing challenges and creates a unique and more structurally advanced metal knee brace frame with a continuous concave cross section throughout the frame.

The curved or concave profile of the metal frame enables inserts into the profile that can yield and adapt to the shape to the user. For example, most prior art orthopedic devices have flat surfaces that merely approximate to a user's anatomy. While users with greater size and fleshy regions are less affected, smaller users' anatomies do not adapt well to or fill out the space defined by flat surfaces, rendering the assistance from the orthopedic device suboptimally effective and/or uncomfortable.

The multi-component frame can have inserts that have a curved surface arranged adjacent to the user's anatomy and which conforms better to the user's anatomy. This arrangement is useful to women and children who may have smaller calves. The adjacent curved structure of the multi-component frame can contour to the curvature of the user's calf rather than merely offering a flat surface, providing a better and more comfortable fit between user and brace.

It is found that some preferred metals and alloys thereof may be expensive to form in ways described above to form an entirety of a frame assembly. According to another embodiment, a frame assembly may comprise segments along a continuous length thereof, generally defined between two endpoints such as at a hinge or a pair of hinges, that are formed from different materials. For example, a first segment may couple to or form part of a first hinge and be constructed from malleable steel or aluminum. Such first segment may be long or shortened by being received by a second segment that may formed from a strong and light structural material but of a material not generally malleable in service, such as a resin-impregnated carbon fiber or fiber-reinforced polymeric material. The second segment attaches to a first end portion of the first segment, and the pair of first and second segments may correspond to a lateral or medial side of a user's leg with a knee brace. The combined structure of the first and second segments may be continuous without interruption.

A third segment of a metal or alloy thereof may have a first end portion securing to the second end portion of the second segment, and may be formed from a different material than the second segment. For example, the third segment may generally correspond to a cuff part of a knee brace generally perpendicular or transverse to the femur or tibia, and may require construction from a malleable yet strong material, such as titanium. A second end of the third segment may secure to a second end of a fourth segment generally opposite to the second segment, along a lateral or medial side of the leg. The fourth segment has a first end securing to a fifth segment coupling to or forming part of a second hinge, so each the fourth and fifth segments may correspond respectively in material selection as the second and first segments, respectively. From the preceding embodiment, the length of the frame assembly comprises the first, second, third, fourth and fifth segments of the frame assembly, generally end-to-end to form the length of the frame assembly.

To accommodate and attach features such as straps to the orthopedic device, means for attaching the features may secure to the frame and generally correspond in strength to the strength of the frame assembly. According to an embodiment, a strap attachment or D-ring is provided in a streamlined manner to mitigate or minimize a strap attachment protruding from the frame without compromising the strength of the strap attachment. Because of constructing the strap attachment, the strength is enhanced over conventional strap attachments in that the embodiment comprises a cable pivotally secured to the frame. The strap attachment may include a coaxially arranged tube along at least a segment of a length of the cable so the tube may rotate about the cable to accommodate movement of a strap tethered thereto. The cable may be constructed from an elongate element such as a wire or braided cable, and both the cable and the tube may be formed from metal.

These and other features, aspects, and advantages of the disclosure will become better understood regarding the following description, appended claims, and accompanying drawings.

BRIEF DESCRIPTION OF THE DRAWINGS

FIG. 11 is a partial schematic sectional view of a lower frame assembly of the multi-component frame of FIG. 10A.

FIG. 12 is a rear partial schematic view of a section of the lower frame assembly in FIG. 11.

FIG. 13 is a partial front view of a strut section of the lower frame assembly in FIG. 11.

DETAILED DESCRIPTION OF VARIOUS EMBODIMENTS

Figure 1:
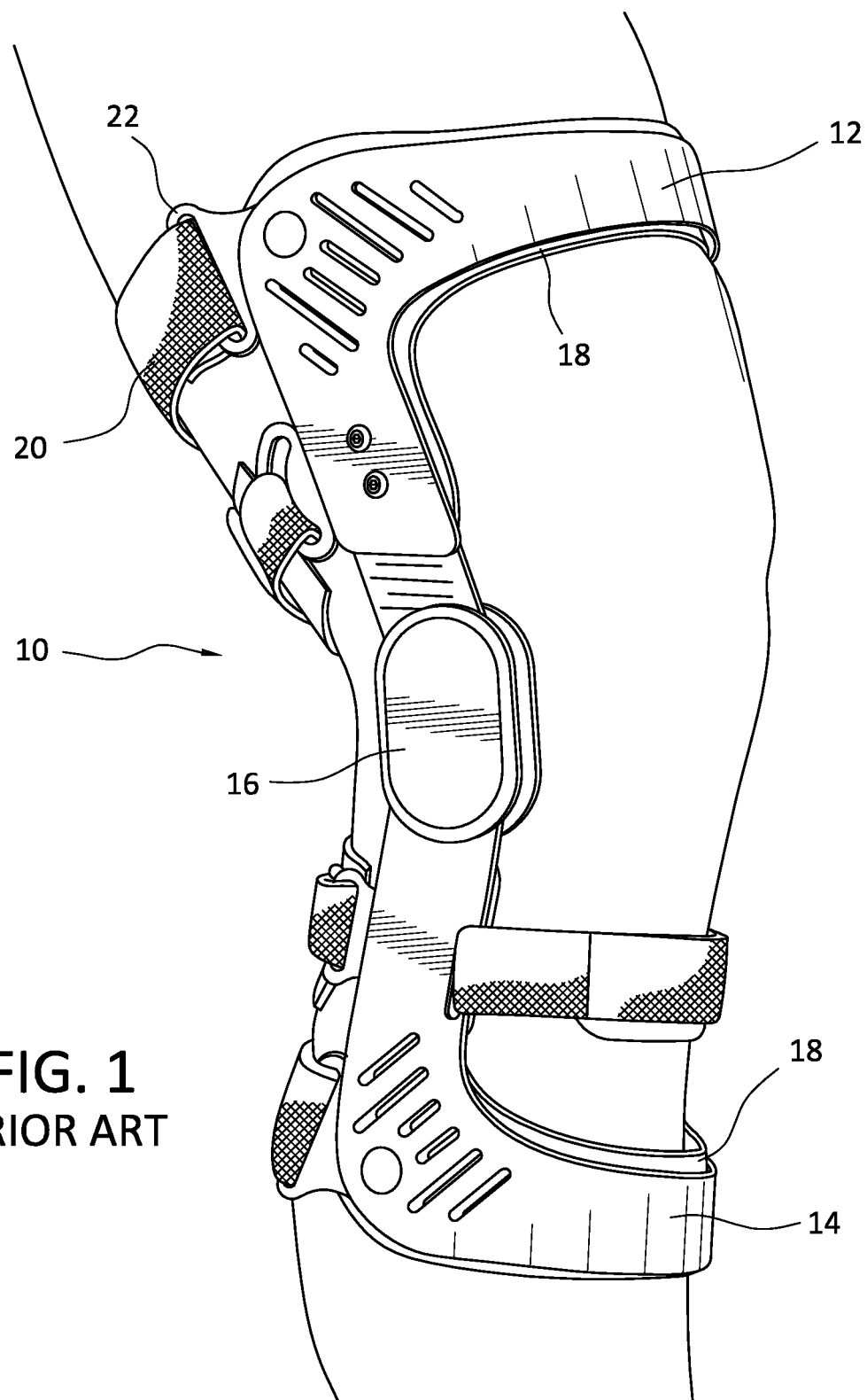
FIG. 1 is a perspective view of a prior art knee brace.

A better understanding of different embodiments of the disclosure may be had from the following description read with the drawings in which like reference characters refer to like elements.

While the disclosure is susceptible to various modifications and alternative constructions, certain illustrative embodiments are shown in the drawings and are described below. It should be understood, however, there is no intention to limit the disclosure to the specific embodiments disclosed, but on the contrary, the intention is to cover all modifications, alternative constructions, combinations, and equivalents falling within the spirit and scope of the disclosure.

Numerical qualifiers (i.e., first, second, etc.) are used in the following discussion merely for explanatory purposes and are not intended to limit their location or the amount of segments or components of the embodiments.

Figure 2:
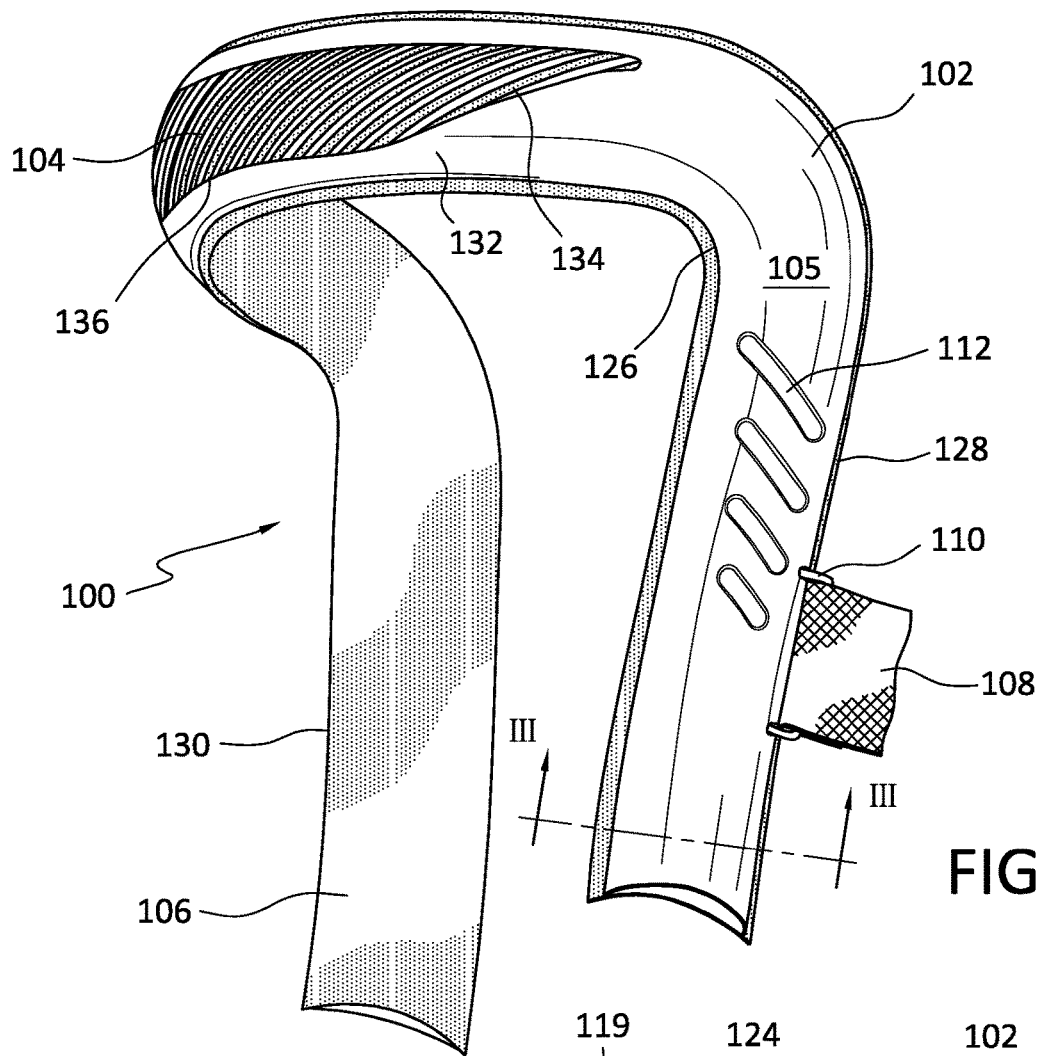
FIG. 2 is a perspective view of an embodiment of a multi-component frame.
Figure 3:
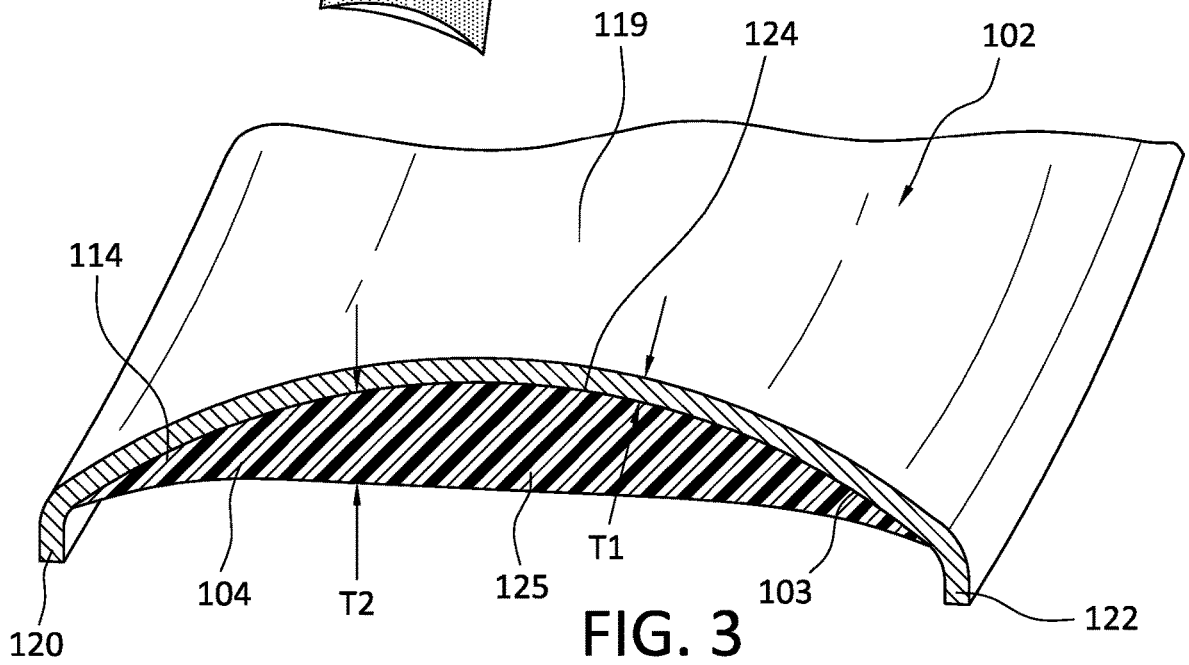
FIG. 3 is a detail view of a cross-section taken along line in FIG. 2.

According to FIGS. 2 and 3, a multi-component frame 100 has a base component 102 comprising edge portions 120, 122 having a different shape than a shape of a main body portion 119. The main body portion 119 defines a concave cross-section 124 and forms a concave portion, or recess 125 adapted to receive additional layers including, but not limited to, a reinforcing layer 104 and padding layer 106.

By "continuous," it is meant that the edge portions 120, 122 and the main body portion 119 can be formed from a single piece without interruptions or sections adhered thereto. The base component 102 may comprise an elongate structure formed according to a predetermined shape so the predetermined shape is formed from the elongate structure in its entirety.

The base component 102 may be made from a rigid structural material, and defines first and second sides 103, 105 and the concave cross-section 124. The base component 102 is constructed from a metal such as a metal alloy including titanium or aluminum. An insert or layer 104 may extend along the first side 103 of the base component 102 and may be constructed from a different material than the base component 102. The insert or layer 104 may be arranged as a reinforcement layer 104. The difference in materials may be provided, so the multi-component frame 100 balances and optimizes the characteristics and benefits of the materials of the base component 102 and the reinforcement layer 104.

The base component 102 may be uniformly formed as having the same cross-sectional profile along lengths of the base component 102, in contrast to corner sections. The base component 102 may likewise have a uniform thickness along its length or may have a variable thickness depending on areas requiring enhanced strength (i.e., corner sections). The base component 102 may define definitive peripheral edges to the multi-component frame by the edge portions or may be adapted with lips, flanges, or other structural features for interlocking with other components, as described in embodiments herein.

The reinforcement layer 104 is not limited to a single layer, but rather may comprise multiple or different layers from different materials depending on their proximity to the base component 102 and according to their specific characteristics. For example, the reinforcement layer 104 may be constructed from a resin-impregnated material including a reinforcement fiber selected from the group of carbon, glass, and Kevlar. This arrangement (the shape and size of the base component 102 and in some embodiments, the provision of a reinforcement layer 104) advantageously allows the strength, weight, and bulk of an orthopedic device comprising the multi-component frame 100 to be optimized, so the weight and profile of the base component 102 may be minimized without sacrificing needed strength. This may beneficially minimize the costs of materials and constructions and improving the comfort for a user (e.g. by reducing the weight of the device).

The first side 103 of the base component 102 may define flanged edge portions 120, 122. The concave cross-section 124 includes a concave portion 125 extending between the flanged edge portions 120, 122. From the contour of the flanged edged portions 120, 122 and the concave cross-section 124, a three-dimensional shape (as opposed to the flat shape and profile of existing frames) is achieved, as the concave cross-section 124 protrudes outwardly away from the flanged edge portions 120, 122, and hence the user's body as the second side 105 defines the outermost surface or section of multi-component frame 100 relative to a user.

Referring further to FIGS. 2 and 3, a thickness T1 separates the first and second sides 103, 105, and is generally uniform along a length of the base component 102. The second side 105 of the base component 102 follows a shape of the first side 103 and extends parallel therewith along a length of the base component 102. The reinforcement layer 104 extends at least along the concave portion 125, and parallel with the length of the base component 102. This arrangement generally results in a uniform shape of the base component 102 at different locations.

Referring again to FIG. 2, the base component 102 may include a first segment 128 extending in a first direction and a second segment 130 generally parallel with the first segment 128, and a curved segment 132 extending between the first and second segments 128, 130, as seen also in FIG. 1. Unlike the prior art frame in FIG. 1 which is substantially flat, the concave cross-section 124 of the multi-component frame 100 in FIG. 2 extends along and through the first, second, and curved segments 128, 130, 132. The curved segment 132 extends generally perpendicular to the first direction, and the reinforcement layer 104 extends continuously along the base component 102 from the first and second segments 128, 130. The first segment 128 defines a corner area 126 at which the curved segment 132 extends away from the first segment 128.

The concave cross-section 124 may be provided along an entirety of the length of the base component 102 extending across the first, second, and curved segments 128, 130, 132 to extend continuously without interruption in an elongate single piece, simplifying use and minimizing production and maintenance costs and issues. In embodiments, the concave cross-section 124 may be provided in discrete locations along the base component 102, such as, for example, along elongate portions of at least one of the first and second segments 128, 130.

The base component 102 may define an opening 136 through which is exposed a surface of the reinforcement layer 104, or another layer, such as the padding layer 106 if arranged adjacent the first side 103 of the base component 102. The opening 136 may reduce material of the base component 102, particularly when less strength and support is required along certain locations of the base component 102, thereby reducing bulk, weight, and cost of the multi-component frame 100. The opening 136 may have a tapering section 134 at an end portion thereof to transition back to portions of the base component 102 without the opening 136. The base component 102 may form at least one recess or aperture 112 along or through the second side 105, respectively, to provide ornamental features, reduced weight, added flexibility, or enhanced breathability.

In alternative embodiments, in place of the opening 136, an indentation may be defined by an outside surface of the base component 102 in which an external reinforcement layer may be disposed for added strength. While portions of the multi-component frame 100 are uniform in thickness, additional layers or thicknesses of reinforcement material may be provided in any section where added strength and rigidity are desired.

As shown in FIG. 3, the reinforcement layer 104 has a first side adjacent the first side 103 of the base component 102. When provided with the reinforcement layer 104, the padding layer 106 extends along the reinforcement layer 104 within at least the concave cross-section 124. The thickness T1 of base component 102 may be less than a thickness T2 of the reinforcement layer 104. The reinforcement layer 104 may be confined within and may fill the concave portion 125. The reinforcement layer 104 may have tapered ends 114 reaching to and being at or above at the flanged edge portions 120, 122.

The arrangement of the multi-component frame 100 in FIGS. 2 and 3 advantageously provides increased mechanical strength, owing to the material and especially the concave profile of the base component 102, while also advantageously providing a concave portion 125 that facilitates the disposition of an additional reinforcement layer 104 and a padding layer 106 (among other possible auxiliary structures), and provides a curvature that facilitates greater conformity of the multi-component frame 100 to a user's individual dimensions, both longitudinally and radially. The curvature overcomes the disadvantages of flat frame elements in existing braces by providing a concave shape and additional padding that better mimic the dynamic dimensions of a user's leg while minimizing cost, weight, and bulk.

This is especially advantageous for users, such as some women and children, for whom existing flat frames are not well-suited, as the frames may not closely and comfortably hug portions of their anatomy, such as at the calf. Children especially stand to benefit from a multi-component frame 100 that is more easily adaptable to their smaller and rapidly changing frames and dimensions, as many doctors and clinicians prefer treating the legs of injured children through orthopedic braces to operating on them, yet existing orthopedic braces fail to account for children's needs.

Figure 4:
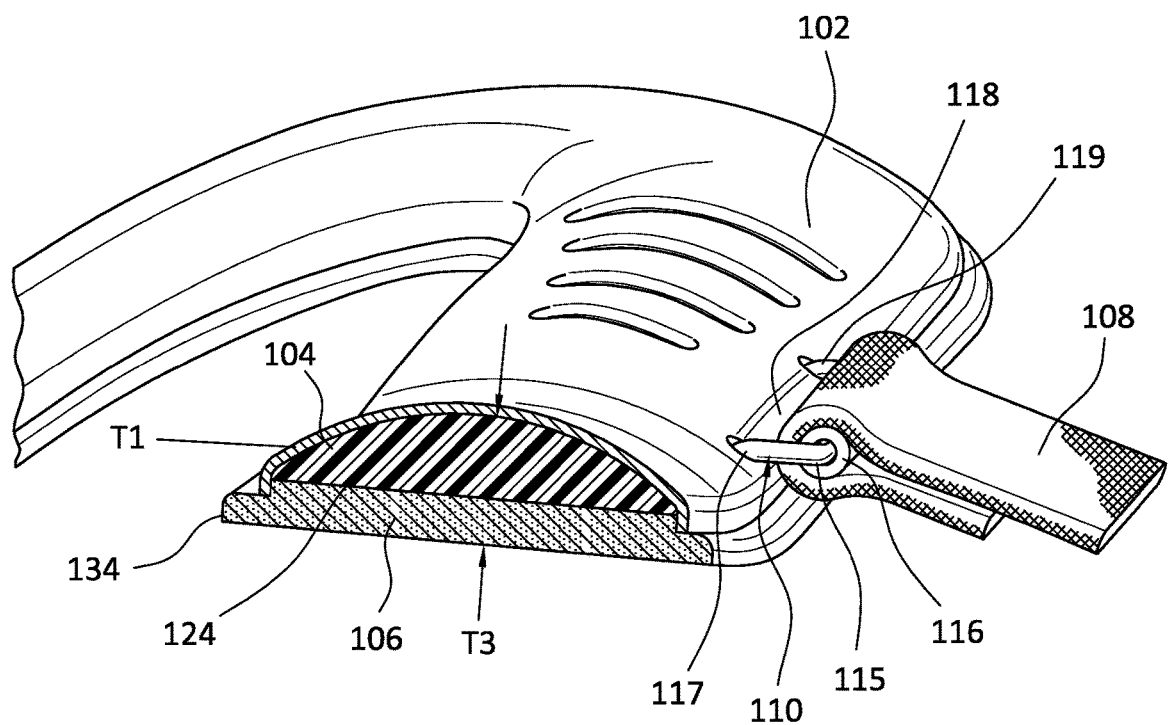
FIG. 4 is an extended view of the cross-section taken along line in FIG. 2.

Turning to FIG. 4, a strap attachment 110 is pivotally attached to the base component 102 and supports a strap 108. The base component 102 may form a recess 118 adapted for receiving the strap attachment 110. The strap attachment 110 comprises a pivotally attached cable 115 having first and second ends 117, 119 pivotally attached to the base component 102. The cable 115 may be formed from an alloy or other suitable metal, polymer, or composite material. A roller 116 is secured to the cable 115 over which the strap 108 secures, and prevents binding of or other interferences with the strap 108.

The configuration of the strap attachment 110 in the recess 118 advantageously reduces bulk and complication of a brace including the multi-component frame 100, as the strap attachment 110 may protrude less outwardly from the base component 102. This feature, combined with using a pivotally attached cable 115 to flexibly secure the strap 108, reduces both the size of the brace and the likelihood of discomfort while still providing needed strength.

FIG. 4 exemplifies how the multi-component frame 100 may only comprise the base component 102 and the padding layer 106. The padding layer 106 extends into the concave cross-section 124 having a thickness T3 greater than the thickness T1 of the base component 102. The padding layer 106 may have edge portions 134 extending laterally beyond the side portions of the base component 102 and/or toward the user beyond the base component 102. By arranging the padding layer 106 within the concave portion 125 defined by the concave cross-section 124, the size and profile of the multi-component frame 100 may be reduced without compromising comfort for a user, as the concave portion allows for a comfortable amount of padding 106 to be provided within the concavity 125 of the base component 102 but without jutting outward therefrom towards a user and thereby increasing a profile of the brace. Padding 106 that can be partially or wholly accommodated within the concavity of the base component 102 is greater (e.g., being thicker and more comfortable) than padding normally and feasibly appended to flat frame components in existing braces.

Figure 5:
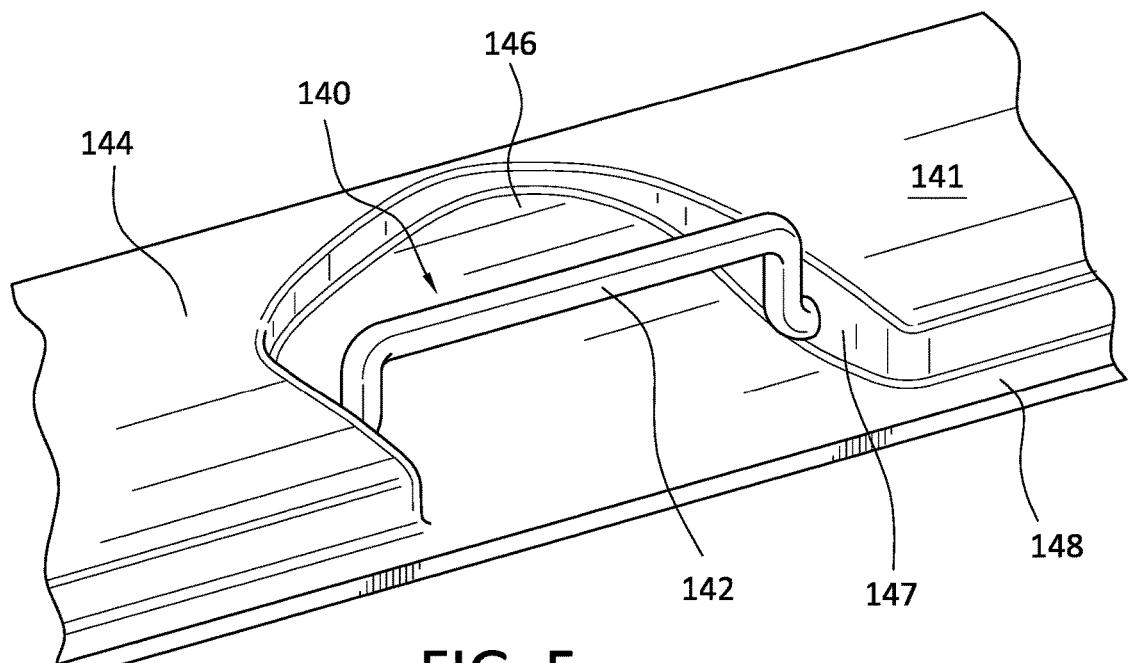
FIG. 5 is a perspective view of a variation of the embodiment of FIG. 2.

FIG. 5 shows a variation of the strap attachment 110 of FIG. 4, with a strap attachment 140 secured along a segment 144 of the multi-component frame 141. In this variation, the strap attachment 140 includes a rigid bar 142 pivotally attached to the segment 144 within a recess 146 formed by the multi-component frame 141. The rigid bar 142 may be formed from a structural material, and may have a geometry and material strength to prevent yielding of a strap 108 looped thereabout and tensioned therefrom. The recess 146 may have a profile to accommodate a shape of a strap portion, head, or segment. The recess 146 may also have a transitional depth 147, with greater depth at where the rigid bar 142 secures to the multi-component frame 141. The transitional depth 147 has the added benefit of helping to guide the strap 108 in a useful direction and prevent migration over the user.

The rigid bar 142 advantageously provides sufficient strength to anchor the strap 108 on the user without jutting outwardly by an inconvenient amount. This minimizes the profile of the multi-component frame 141 and is enabled by the recess 146.

A peripheral edge of the recess 146 may be recessed to form a flange 148 to ease the transition of the multi-component frame 141 against the user, and enable smooth rollover of the strap 108 over the peripheral edge of the multi-component frame 141 to better conform to the body of the user.

Figure 6:
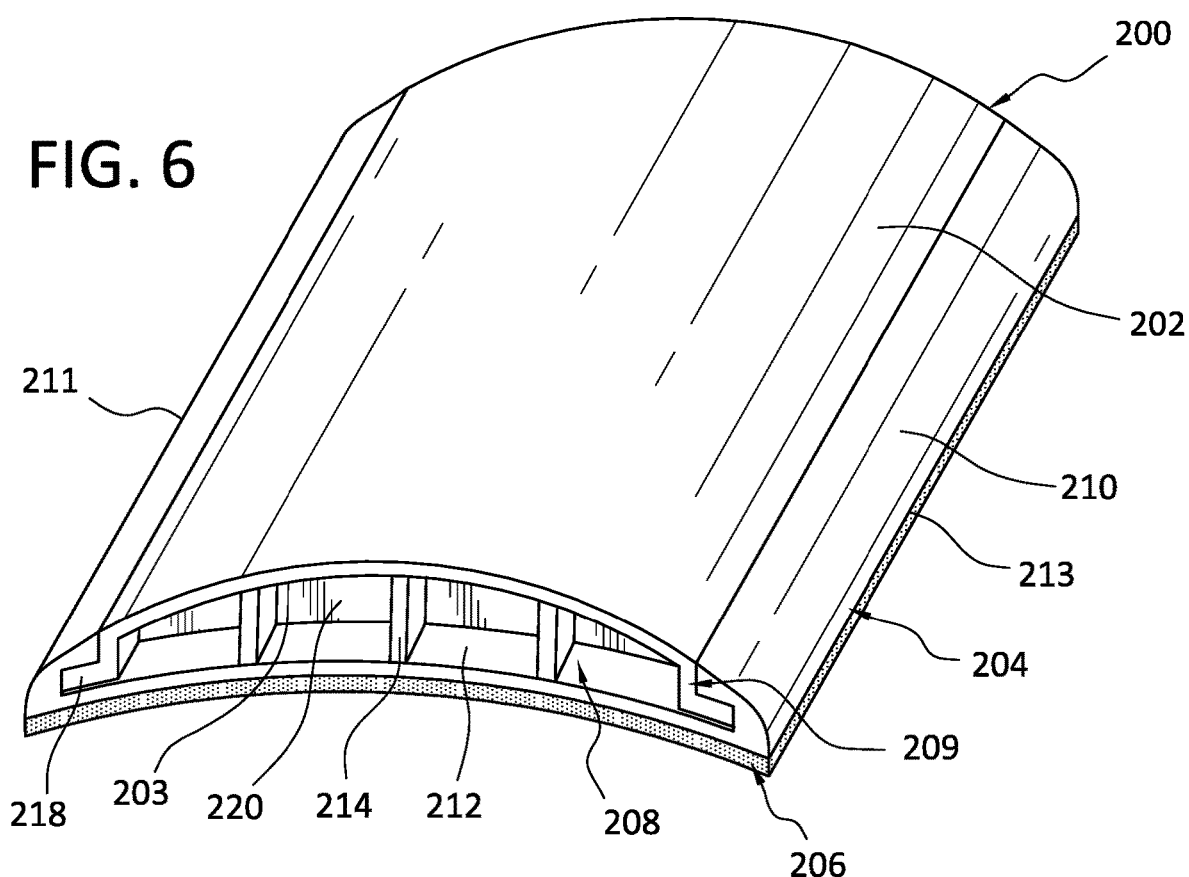
FIG. 6 is a perspective view of a segment of another embodiment of a multi-component frame.

FIG. 6 illustrates another embodiment of a multi-component frame 200. The multi-component frame 200 has a base component 202 forming a concave cross-section 203 in and/or to which an insert 204 is provided and interlocks with ledges or flanged arrangements 218 formed by the base component 202. The base component 202 may be made from a structural material such as steel, aluminum, titanium, or other suitable metals and alloys, or fiber-reinforced composite, whereas the insert 204 may be formed from a polymeric material such as a thermoplastic elastomer.

A liner layer 206 may be a fabric layer located along a surface of the insert 204, and intended to be adjacent the user. The liner layer 206 may provide cushioning, reduce migration, and improve comfort to the user. The liner layer 206 may be breathable, and have frictional properties. The liner may facilitate breathability by defining structures that promote airflow, such as heat and fluid transfer, while still cushioning the user's limb. The liner layer 206 may be removable for customization, replacement, and/or cleaning. For example, the liner layer may be arranged with a surface as described in U.S. Pat. No. 8,425,441, granted on Apr. 23, 2013, and incorporated herein by reference.

Figure 7:
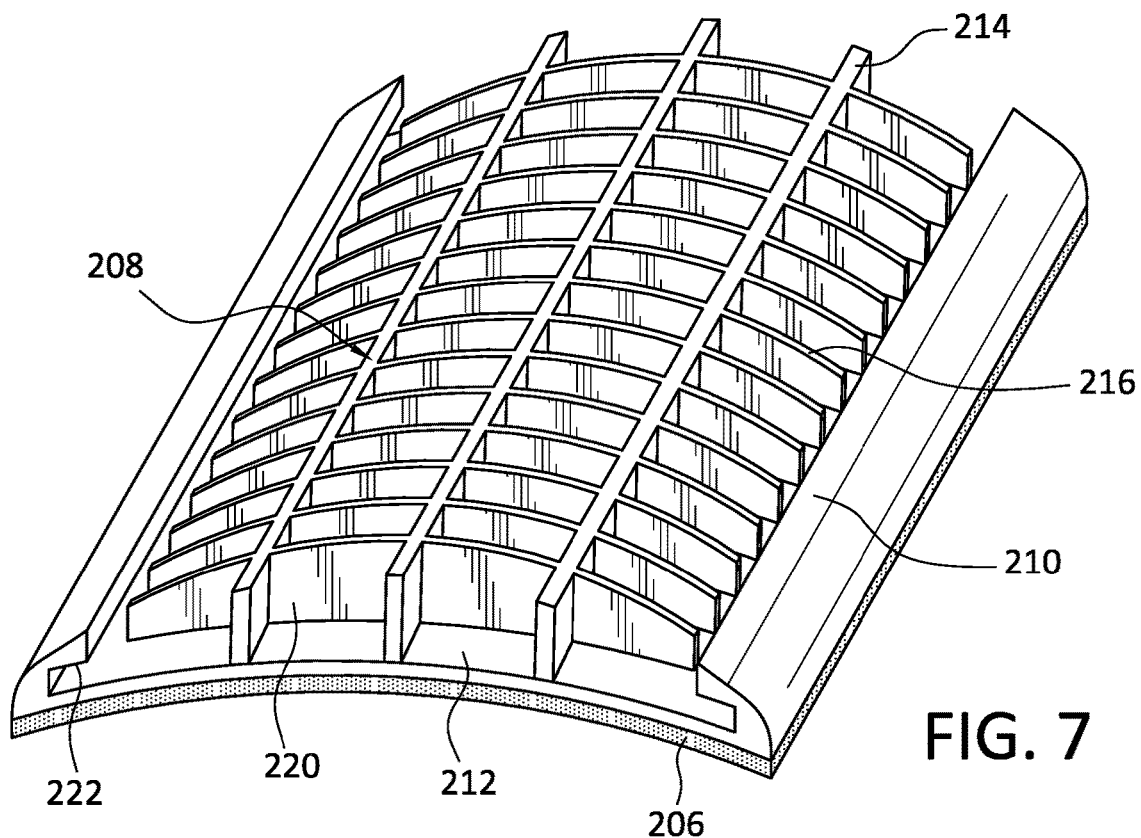
FIG. 7 is a perspective view of an insert in the multi-component frame of FIG. 6.

As shown in FIGS. 6 and 7, the insert 204 may form a structure 208 adapted to accommodate the user's anatomy with sufficient rigidity while yielding in part to the user's anatomy and movement. In an exemplary embodiment, the structure 208 forms an open-grid formation along a first side of the structure 208 that corresponds to the concavity of the brace component 202. The open-grid formation forms first and second sets of rows 214, 216 with voids 220 located therebetween. The structure 208 may define a second surface 212 that may be continuously closed and along which the liner layer 206 secures.

The insert 204 is interlocked with an edge configuration 209 of the base component 202, whereby the insert 204 has an edge profile 210 that extends over the edge configuration 209. The edge profile 210 extends to both sides 211, 213 of the insert 204, and the second surface 212 extends between the sides 211, 213. The edge configuration 209 may define at least one ledge or flanged arrangement 218 depending from opposed sides of the base component 202, and extending into a corresponding opening 222 of the insert 204. The material difference of the insert 204 and the base component 202 provides a softer and more comfortable edge over the more rigid material of the base component 202.

The edge profile 210 reduces irritation caused by substantially hard or sharp edges of the base component 202 and allows the base component 202 to at least partially conform to the anatomy of the user by the edge profile 210. The body of the insert 204 with the structure 208 provides a compliant interface between the edge profile 210 and the base component 202 and serves as a platform for the inner layer 206.

Figure 8:
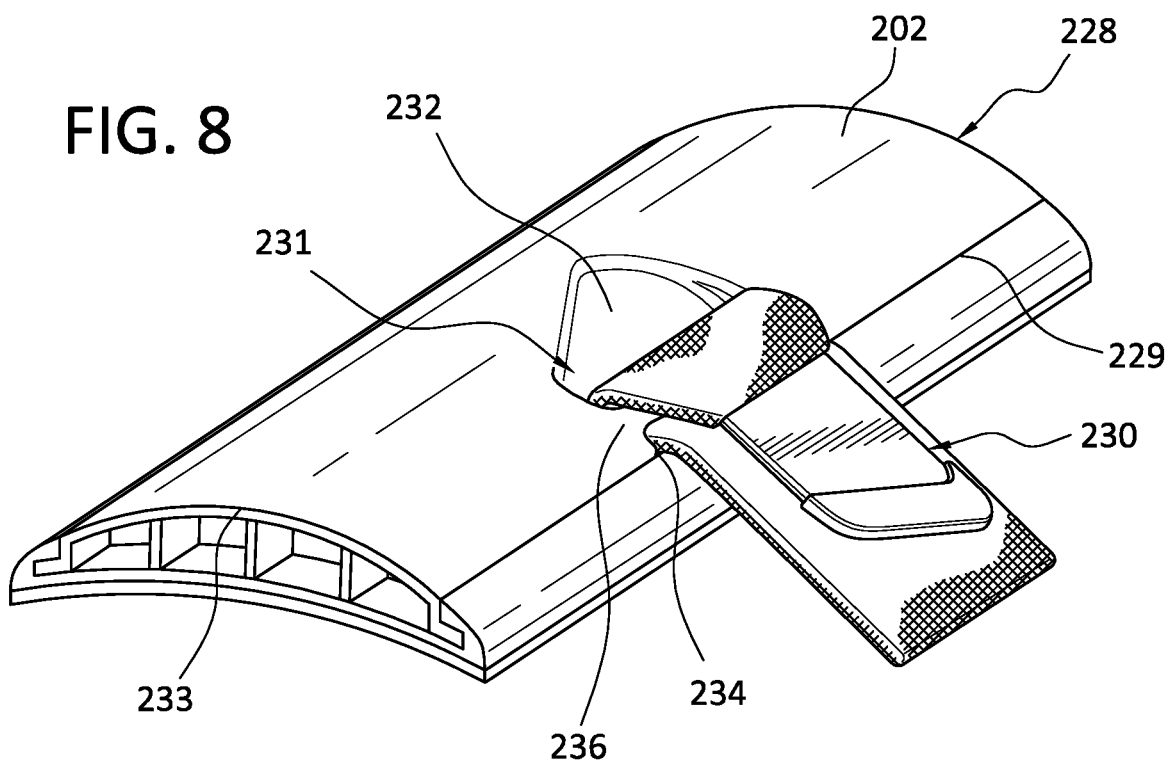
FIG. 8 is a perspective view of a variation of the segment of FIG. 6.

FIG. 8 exemplifies another frame segment 228 for a multi-component frame according to the disclosure and including an integrated strap retainer 231. By "integrated," it should mean that the integrated strap retainer 231 may be formed by the base component 202, in both structure and material. The integrated strap retainer 231 is continuous because it is formed by the base component 202. For example, the integrated strap retainer 231 forms a recess 232 within an exterior surface 233 of the base component 202 over which a bar 236 extends from opposed sides of the recess 232 continuously with the material of the base component 202. The bar 236 possesses the strength of the base component 202, ensuring a secure attachment for a strap with minimized maintenance and assembly issues. The bar 236 may be formed from the material of the base component 202, or may be welded onto the base component 202 and suspended over the recess 232.

The bar 236 may not extend outwardly beyond a periphery of the frame segment 228 and offers a low-profile, sleek, and intuitive integrated strap retainer 231 without the necessity of additional components beyond the mere body and structure of the frame segment 228. The recess 232 has an outlet 234 proximate the edge 229 of the frame segment 228 that transitions or slopes to the edge 229 and over an edge profile of an insert. In this manner, a strap 230 can be secured to and extend outwardly from the frame element 228 without significantly protruding either upwardly or laterally beyond the periphery of the frame segment 228, without compromising structural strength or convenience of the strap, frame, or brace.

Figure 9:
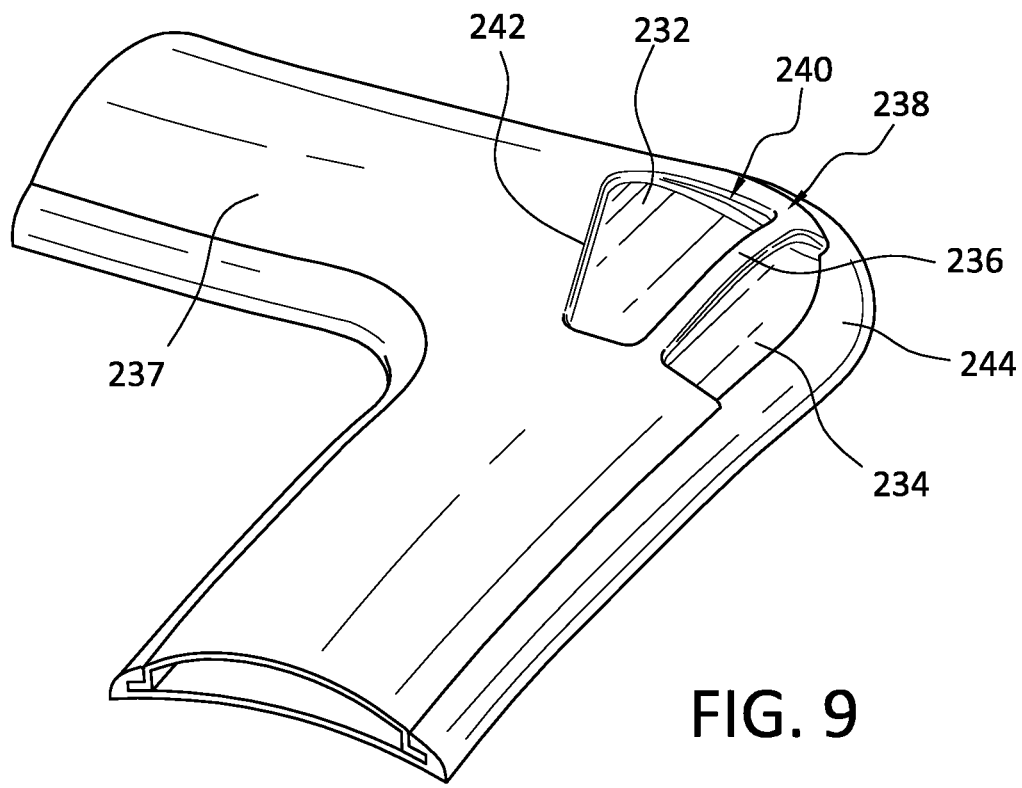
FIG. 9 is a perspective view of a corner segment of a multi-component frame.

FIG. 9 illustrates a variation of the integrated strap retainer 240 located at a corner 238 of a frame segment 237. The integrated manner of the integrated strap retainer 240 in FIG. 9, or the integrated strap retainer 231 in FIG. 8, has the advantage of customizing the location of the integrated strap retainers 231, 240 along locations of frame segments without the necessity of additional components, and can limit the extent by which straps extend from the frame segments. The recess 232 comprises a transition portion 242 extending from an interior portion of the exterior surface 233 of the base component 202 to an edge portion 244. The transition portion 242 facilitates a sleek, aesthetically pleasing, and intuitive functionality of the integrated strap retainer 240 by visually and tactilely guiding a user or clinician to the bar 236.

According to another embodiment in FIGS. 10A-15, an orthopedic device 300 has first or upper and second or lower frame assemblies 301, 303. Each of the upper and lower frame assemblies 301, 303 comprises segments along a continuous length, L1, L2, respectively thereof, generally defined between two endpoints such as at a hinge or a pair of hinges 308, 309. The endpoints are not limited to hinges, and may be simply whereat a corresponding frame assembly terminates. The frame segments in and defining the continuous length L1, L2 of each of the first or upper and second or lower frame assemblies 301. 303 are formed from at least two materials.

Using the second or lower frame assembly 303 for example, a first segment 320 may couple to or form part of a first hinge 308 and be constructed from steel, aluminum or other suitable material for forming part of the first hinge 308. For example, the first segment 320 is a hinge element or strut. While in FIG. 11 the first segment 320 defines a hinge head 344, such first segment 320 is not limited to such structure. The first segment 320 may be long or shortened by being received by a second segment 312 that may be formed from a strong and light structural material but of a material not generally malleable in service, such as a resin impregnated carbon fiber or fiber-reinforced polymeric material. The second segment 312 may be an elongate strut, generally parallel with the leg. The second segment 312 attaches to a first end portion of the first segment 320, and the pair of first and second segments 320, 312 may correspond to a lateral or medial side of a user's leg with a knee brace. The combined structure of the first and second segments 312, 320 may be continuous without interruption.

A third segment 310, such as being formed from a metal or alloy, may have a first end portion securing to the second end portion of the second segment 312, and may be formed from a different material relative to the second segment 312. For example, the third segment 310 may generally correspond to a cuff part of a knee brace generally perpendicular or transverse to a femur or tibia, and may require construction from a malleable yet strong material, such as titanium. The strength of the third segment 310 may be enhanced by having a three-dimensional shape in contrast to a flat configuration, and may be contoured as in preceding embodiments. By limiting the length of the third segment 310, the cost of using an expensive material such as titanium may be minimized and located in a focused manner to where it may be most required, while using less expensive materials, such as materials forming the first and second segments which require less strength or customizability.

A second end of the third segment 310 may secure to a second end of a fourth segment 314 generally opposite to the second segment 312, arranged along an opposed lateral or medial side of the leg. The fourth segment 314 has a first end securing to fifth segment 322 coupling to the second hinge 309, so each the fourth and fifth segments 314, 322 may correspond respectively in material selection as the second and first segments 312, 320, respectively. From the preceding embodiment, the length of the frame assembly comprises the first, second, third, fourth and fifth segments 320, 312, 310, 314, 322 of the second or lower frame assembly 303, generally connected end-to-end to form the length L2 of the second or lower frame assembly 303.

Figure 14:
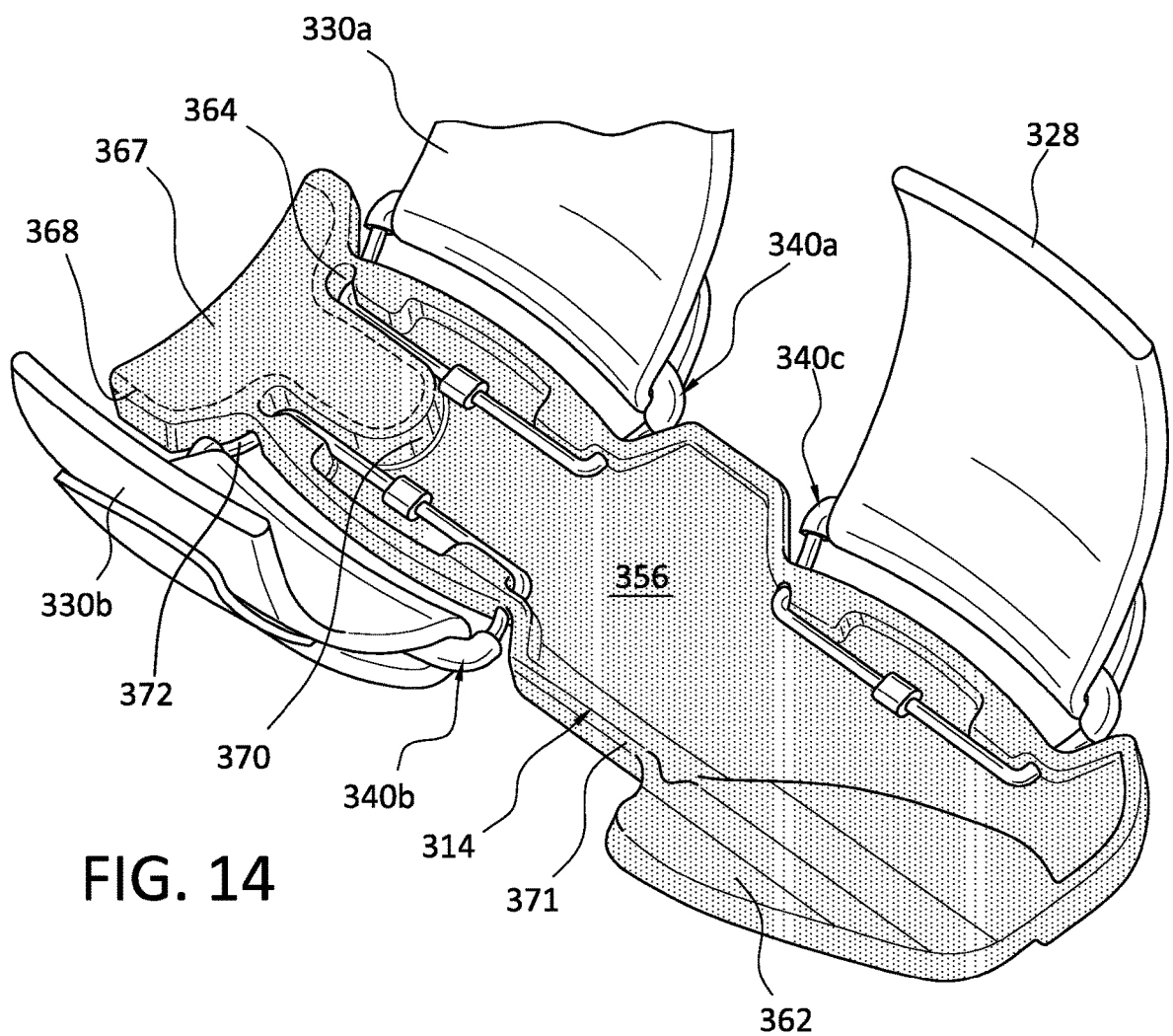
FIG. 14 is a partial rear view of the strut in FIG. 11 including straps and D-rings.
Figure 15:
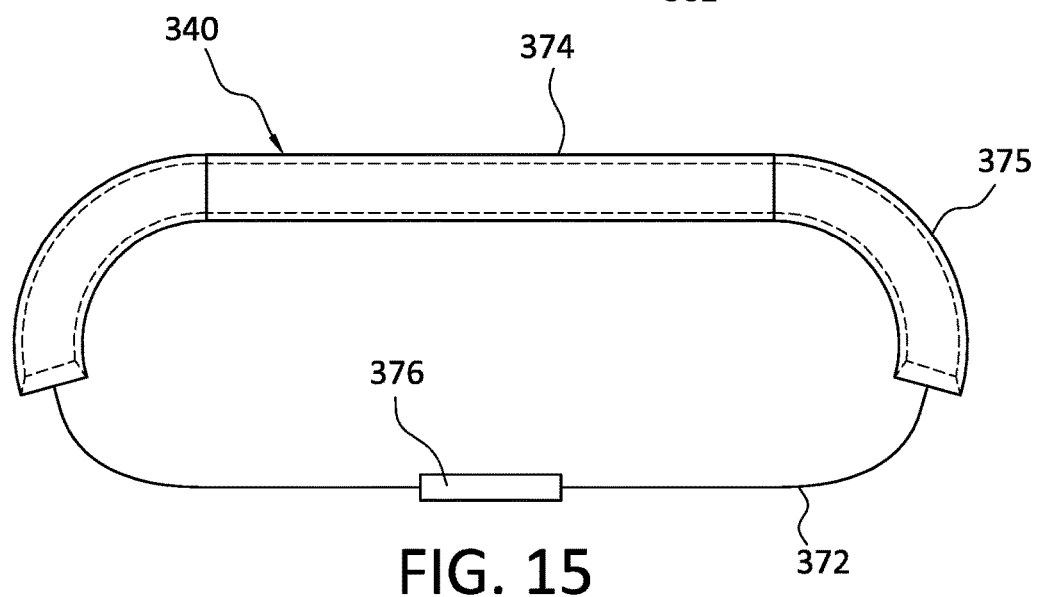
FIG. 15 is a plan view of the D-ring in FIG. 14.

By "being connected end-to-end," it is indicated that the segments are at least connected to one another at their ends, but embraces the segments overlapping one another and extending along one another segment's individual length, such as having overlapping portions in FIGS. 12 and 13, or a slot connection in FIG. 14. The segments may be fastened to one another, as exemplified by fasteners in FIGS. 10A and 10B, and FIG. 12 to secure to one another as with fasteners 336, 338. Alternative ways for securing segments may include adhesives or other bonding techniques and means, and the ways for securing the segments may be permanent or removable.

The first or upper frame assembly 301 similarly includes a first segment 316, a second segment 304, a third segment 302, a fourth segment 306 and a fifth segment 318 corresponding generally to constructing the second or lower frame assembly 303. While the depicted embodiment shows similarity in construction of the first or upper frame assembly 301 and the second or lower frame assembly 303, embodiments are not limited to such similarity. For example, either of the first or upper frame assembly 301 and the second or lower frame assembly 303 may have a different number of segments or may have only a sole segment.

Figures 10A, 10B:
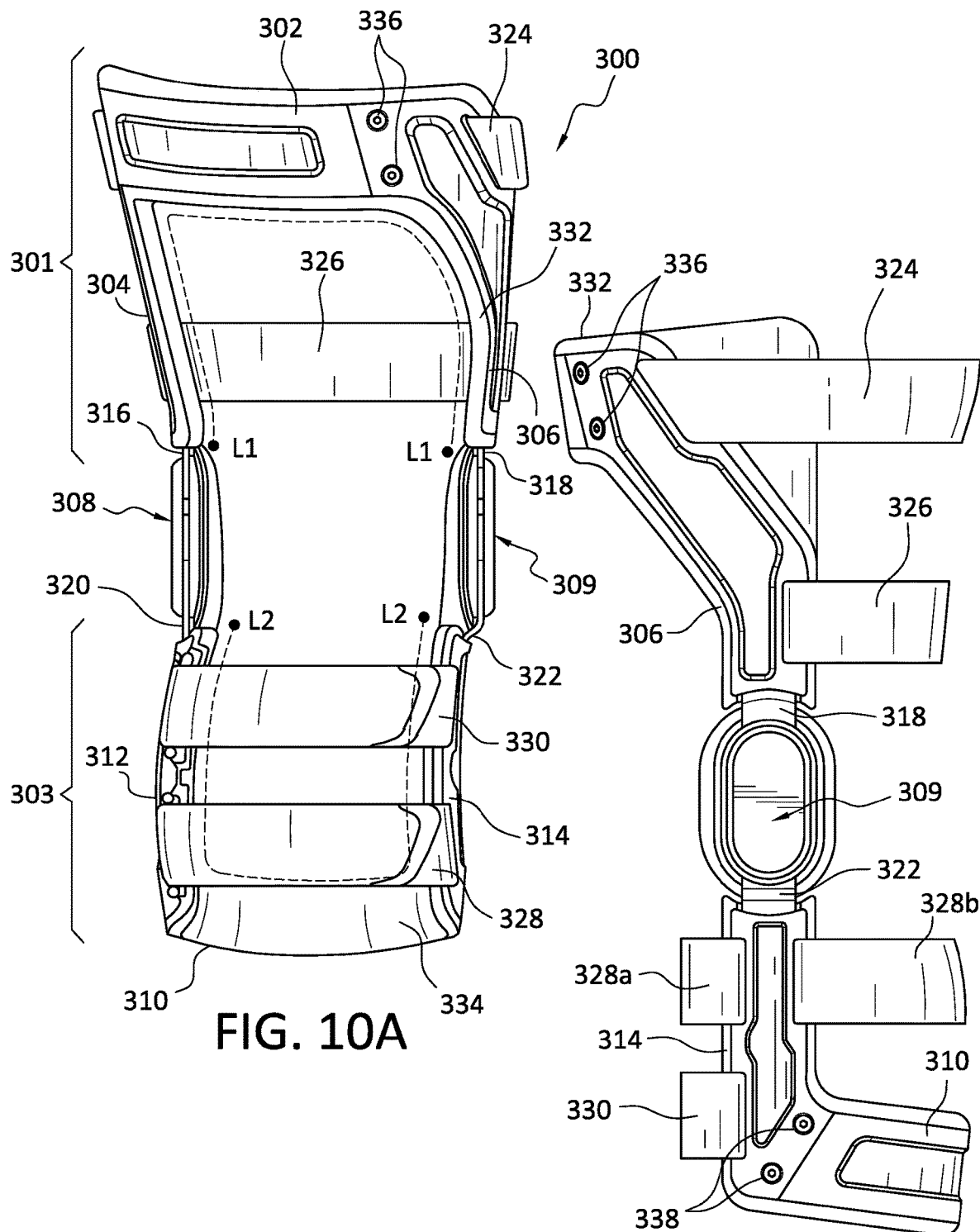
FIG. 10A is a front elevational view of a knee brace having a multi-component frame.
FIG. 10B is a side elevational view of the knee brace of FIG. 10A.

The multi-component orthopedic device of FIGS. 10A and 10B is advantageous over known orthopedic devices. Unlike prior art braces that employ a same material throughout the length of the frame of the orthopedic device. While in such prior art braces providing stiff struts may be expensive or heavy, they lack means for selectively balancing strength and comfort. Rather, one of strength and comfort is often compromised to yield one quality more than the other.

It has been found that when there is a stiff strut, as in the embodiment of FIGS. 10A and 10B, the second and fourth segments or struts made from a material such as resin impregnated fiber or similar material, and the third segment or cuff may be made to be more flexible due to the material selection and/or geometry, while still maintaining the strength of the orthopedic device. A more flexible cuff, at least relative to the strut, yields a more comfortable knee brace, without compromising strength of the orthopedic device The orthopedic device offers the same level of protection but does so in balancing strength and comfort by selecting appropriate materials and/or geometries for different segments of the orthopedic device, which cannot be achieved when a single material frame is employed.

In the aforementioned embodiments, when the first, second and third segments are constructed of different materials for their intended purpose and function (i.e., stiffness for the strut or second segment and flexibility for the cuff or third segment), if a "malleable" or "adjustable" brace is desired, at least the gear extending to the hinge and the cuff should be malleable. Normally offering only one of the gear and cuff as being malleable cannot qualify as a malleable brace. By interposing a stiff strut between the first segment and third segment, each preferably having different material properties and being of stiffness lower than the strut, the orthopedic device can qualify as a malleable brace while offering the aforementioned improved stiffness provided by a resin impregnated fiber or similar material strut.

While the segments are described as being constructed from different materials, different segments may be adapted geometrically to having different properties, as compared to a frame having a single-material construction and generally consistently sized and configured segments. For example, the second segment may have strengthening means, such as ribs or a three-dimensional or arcuate cross-section that makes the segment stronger over other segments if maintained of the same material and generally same dimensions and configuration without the strengthening means. The third segment may be sized and configured different from an adjacent segment making it distinctly more flexible than the second segment. The third segment may still be sized and configured with strengthening means, however the second segment or strut may be stiffer.

FIG. 11 exemplifies an outer section of the lower frame assembly including the fifth segment 322 defined as a hinge element. The fifth segment 322 includes an extension 342 forming a second end portion and is received by a slot 368 defined by at a first end portion 367 of a fourth segment 314.

The fifth segment 322 forms a hinge head 344 forming a first end portion and is adapted to mesh with a corresponding hinge head of the upper frame assembly (not shown). The fifth segment 322 may be constructed from a variety of suitable materials for a hinge assembly.

As exemplified by FIG. 12, the fourth segment 314 is generally elongate from the first end portion 367 to a second end portion 369 securing to a first end 371 of the third segment 310. The fasteners 338a, 338b may be defined as posts 354a, 354b connecting to a side of the third segment 310 and extending through apertures 352a, 352b configured and dimensioned for receiving the posts 354a, 354b. The posts 354a, 354b may be formed by or secured to the third segment 310. For example, the fasteners 338a, 338b may be accessible from an outside of the lower frame assembly, as in FIGS. 10A and 10B, or may only secure to an inside of the lower frame assembly 303.

FIG. 13 shows how the first end 371 of the third segment 310 overlaps a landing 362 formed by the second end 369 of the fourth segment 314. The landing 362 may be a thinned section relative to a nominal thickness 358 of the fourth segment 314.

FIGS. 11 and 12 shows how the fourth segment 314 has a peripheral edge 348 colinear and continuous with a peripheral edge 349 of the third segment 310. Both the first or upper frame assembly and the second or lower frame assembly each include liners 332, 334 extending along an inner surface and over peripheral edges. FIG. 11 illustrates how a peripheral edge of a liner 350 may extend over the coextensive peripheral edges 348, 349 as in preceding embodiments. Likewise, the third segment 310 may have openings 346 or be three-dimensionally formed as in preceding embodiments.

FIG. 14 illustrates an inner side of the fourth segment 314 with the liner removed. To accommodate and attach features to the orthopedic device, such as straps 324, 326, 328a, 238b, 330a, 330b, means for attaching features may secure to the frame and generally correspond in strength to the strength of the frame assembly.

According to an embodiment, a strap attachment or D-ring 340 is provided in a streamlined manner to mitigate protruding from the frame, such as at the fourth segment 314, without compromising the strength of the strap attachment. Because of constructing the strap attachment, the strength is enhanced over conventional strap attachments in that the embodiment comprises a cable 372 pivotally secured to the fourth segment 314. The strap attachment 340 includes a coaxially arranged tube 374 along at least a segment of a length of the cable 372 so the tube 374 may rotate about the cable 372 to accommodate movement of a strap tethered thereto.

Ends of the cable 372 may be secured to one another by a connector 376 so the cable 372 can be a continuous loop. The cable 372 may be formed from an elongate element such as a wire or a braided cable, and may be formed from metal or polymeric material such as nylon. The tube 374 may be formed from metal or a polymeric material, and may have radial end portions 375 to retain and reinforce a strap. The cable may be replaced with a tubular member having a continuous structure formed or shaped as a loop to accommodate a tube or may be provided with or without such tube.

The fourth segment 314 may have a cavity 356 to accommodate the strap attachment 340 which may comprise individual strap attachments 340a, 340b, and 340c. For example, the cavity 356 has a biasing form 370 to retain strap attachments such as the cable 372. The fourth segment 314 preferably includes apertures 364 through which the strap attachment 340 extends, and may be provided to retain the cable 372 in position relative to the fourth segment 314 or enlarged to allow for pivoting relative to the fourth segment 314. The tube 374 is adapted to extend outwardly relative to a periphery 371 of the fourth segment 314. The periphery 371 may include recesses to maintain the strap attachment 340 close to the fourth segment 314 and contribute to a streamlined configuration.

The strap attachment 340 with the cable 372 and tube 374 offers a stronger strap attachment over conventional D-rings, particularly those constructed from a simple metal ring or a plastic D-ring. As the cable 372 and tube 374 may be constructed from metal, the strap attachment 340 also enables smaller and thinner components to retain a strap. The strap attachment 340 can be closely secured to the frame so at to closely approximate a periphery of the frame, as shown in FIGS. 10A and 10B and FIGS. 12 and 14.

These and other embodiments of the present disclosure overcome the deficiencies of existing frames for braces by providing a multi-component frame that reduces bulk and weight without sacrificing needed strength and provides adjustability for a user's specific dimensions. The advantageous three-dimensional configuration of the multi-component frame (as opposed to the flat configuration of frames in existing braces), with depending edge portions and a concave portion, provides both mechanical strength and a recess wherein additional support material, auxiliary structures, and/or padding may be discreetly and conveniently disposed.

While the foregoing embodiments have been described and shown, it is understood that alternatives and modifications of these embodiments, such as those suggested by others, may be made to fall within the scope of the disclosure.

The invention claimed is:

1. A frame in an orthopedic device, comprising:
a first component made from a structural metal material, the first component defining first and second sides, the first and second sides being coextensive and parallel so as to form a concave cross-section bounded by first and second flanged edge portions extending from opposed sides of the concave cross-section and linearly from the concave cross-section;
a second component connected to the first component and having a non-metal material composition from the first component, the second component having a first surface lining an inside of the concave cross-section short of the first and second flanged edge portions, and a second surface opposite the first surface, wherein the second component is constructed from a resin-impregnated material including a plurality of reinforcement fibers; and
a strap retainer attached to the first component and arranged for supporting a strap; wherein the first component forms a recess adapted for receiving the strap retainer.

2. The frame of claim 1, wherein the strap retainer is formed by the structural metal material and integrated with the first component, the strap retainer extending within the recess, the strap retainer configured and dimensioned for supporting the strap.

3. The frame of claim 2, wherein the strap retainer forms a bar extending from opposed sides continuously within the recess of the first component, the bar being suspended over the recess to form a clearance therewith arranged for h strap to extend therethrough.

4. The frame of claim 3, wherein the bar extends solely within the recess and is arranged not to extend outwardly beyond an edge of a periphery of the first component.

5. The frame of claim 4, wherein the recess defines an outlet proximate the edge of the first component, the recess having a depth transitioning and reducing to the edge and is configured and dimensioned for the strap to be secured to and extend outwardly from the first component without protruding either upwardly or laterally beyond the periphery of the first component.

6. The frame of claim 1, wherein the strap retainer includes a wire having first and second ends pivotally attached to the first component, the wire being formed from an alloy or other metal, polymer, or composite material.

7. The frame of claim 6, wherein the strap retainer further includes a roller secured to the wire and arranged for a strap to extend thereover.

8. The frame of claim 6, wherein the recess is defined about an exterior surface of the first component into which the strap retainer extends and receives the strap.

9. The frame of claim 1, wherein the second side follows a shape of the first side and extends parallel therewith along a length of the first component.

10. The frame of claim 9, wherein a thickness separates the first and second sides, and is uniform along the length of the first component.

11. The frame of claim 1, wherein the first component is constructed from a metal alloy.

12. The frame of claim 1, wherein a thickness separates the first and second sides, and is uniform along the length of the first component.

13. The frame of claim 1, wherein the plurality of reinforcement fibers is selected from the group consisting of carbon, glass, and para-aramid synthetic fibers.

14. The frame of claim 1, wherein the first component includes a first segment extending in a first direction and a second segment parallel with the first segment, a curved segment extending between the first and second segments and perpendicular to the first direction such that the second component extends continuously along the first component from the first and second segments.

15. The frame of claim 1, further comprising a padding layer extending along the second surface of the second component and beyond the first and second flanged edge portions so as to form edge portions extending laterally beyond the first and second flanged edge portions.

16. A frame in an orthopedic device, comprising:
a first component made from a structural material, the first component defining first and second sides, the first and second sides being coextensive and parallel so as to form a concave cross-section bounded by first and second flanged edge portions extending from opposed sides of the concave cross-section and linearly from the concave cross-section, wherein the first component is constructed from a metal alloy;
a second component connected to the first component and having a different material composition from the first component, the second component having a first surface lining an inside of the concave cross-section short of the first and second flanged edge portions, and a second surface opposite the first surface, wherein the second component is constructed from a resin-impregnated material including a plurality of reinforcement fibers;
a strap retainer attached to the first component and arranged for supporting a strap; wherein the first component forms a recess adapted for receiving the strap retainer.

17. The frame of claim 16, further comprising a padding layer extending along the second surface of the second component and beyond the first and second flanged edge portions so as to form edge portions extending laterally beyond the first and second flanged edge portions.

18. A frame in an orthopedic device, comprising:
a first frame segment formed by a structural material, the first frame segment defining interior and exterior sides such that the interior side is configured to face a limb of a user, the first frame segment forming a recess along the exterior side thereof, the first frame segment defining first and second sides, the first and second sides being coextensive and parallel so as to form a concave cross-section bounded by first and second flanged edge portions extending from opposed sides of the concave cross-section and linearly from the concave cross-section;
a second frame segment connected to the first frame segment formed by a different structural material composition from the first frame segment, the second frame segment having a first surface lining an inside of the concave cross-section short of the first and second flanged edge portions, and a second surface opposite the first surface, wherein the second frame segment structural material composition is constructed from a resin-impregnated material including a plurality of reinforcement fibers;
a strap retainer formed by the structural material of the first frame segment and integrated with the first frame segment, the strap retainer extending within the recess, the strap retainer configured and dimensioned for supporting a strap;
wherein the strap retainer forms a bar extending from opposed sides continuously within the recess of the first frame segment, the bar being suspended over the recess to form a clearance therewith arranged for the strap to extend therethrough;
wherein the bar extends solely within the recess and is arranged not to extend outwardly beyond an edge of a periphery of the first frame segment;
wherein the recess defines an outlet proximate the edge of the first frame segment, the recess having a depth transitioning and reducing to the edge and is configured and dimensioned for the strap to be secured to and extend outwardly from the first frame segment without protruding either upwardly or laterally beyond the periphery of the frame segment.

* * * * *